United States Patent
Dubrul et al.

(10) Patent No.: US 6,325,812 B1
(45) Date of Patent: *Dec. 4, 2001

(54) TROCAR SYSTEM HAVING EXPANDABLE PORT

(75) Inventors: William R. Dubrul, Redwood City; Craig K. Tsuji, Sunnyvale; John E. Carlson, Mountain View, all of CA (US)

(73) Assignee: Innerdyne, Inc., Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/477,227

(22) Filed: Jan. 4, 2000

Related U.S. Application Data

(60) Continuation of application No. 08/424,696, filed on Apr. 19, 1995, now Pat. No. 6,080,174, which is a division of application No. 08/026,922, filed on Mar. 5, 1993, now Pat. No. 5,431,676.

(51) Int. Cl.⁷ .................................................. A61B 17/34
(52) U.S. Cl. ...................... 606/185; 606/191; 604/164.01
(58) Field of Search .................................... 604/160, 161, 604/164–169, 185, 188, 246–248, 264, 272, 274, 281, 164.01, 164.03, 164.06, 164.1, 171, 263; 606/191, 184, 185, 198; 600/564

(56) References Cited

U.S. PATENT DOCUMENTS

| | | |
|---|---|---|
| 668,879 | 2/1901 | Miller . |
| 1,213,001 | 1/1917 | Philips . |
| 1,248,492 | 12/1917 | Hill . |
| 2,548,602 | 4/1951 | Greenburg . |
| 3,545,443 | 12/1970 | Ansari . |
| 3,742,958 | 7/1973 | Rundles . |
| 3,789,852 | * 2/1974 | Kim et al. ........................... 606/198 |
| 3,902,492 | 9/1975 | Greenhalgh . |
| 4,018,230 | 4/1977 | Ochiai et al. . |
| 4,141,364 | 2/1979 | Schultze . |

(List continued on next page.)

FOREIGN PATENT DOCUMENTS

| | | |
|---|---|---|
| 0 177 177 | 4/1986 | (EP) . |
| 0 385 920 | 2/1990 | (EP) . |
| WO 92/19312 | 11/1992 | (WO) . |

OTHER PUBLICATIONS

Product brouchure ENDOMED™, Cooper Surgical Inc. (1992) 2 pages.

(List continued on next page.)

Primary Examiner—Henry J. Recla
Assistant Examiner—William Lewis

(57) ABSTRACT

An apparatus and method for forming and enlarging percutaneous penetrations comprises an elongate dilation member which receives an elongate expansion member in an axial lumen thereof. The dilation tube includes a tubular braid which usually comprises a mesh of non-elastic filaments which are radially expandable from a small diameter configuration to a large diameter configuration and which is optionally covered by a removable sheath. The dilation tube is percutaneously introduced to a target site within a patient's body, usually within the abdomen in a laparoscopic procedure. The sheath (if present) is then removed, and the tubular braid thereafter radially expanded by axial insertion of the expansion member through its lumen. The tubular braid is anchored by axial shortening of the mesh and remains in place to permit subsequent exchange of dilation members to provide for different diameter access lumens. Trocar valves may be removably attached to the proximal end of the expansion member to permit the apparatus to be used as a trocar system in laparoscopic procedures where the patient's abdomen has been insufflated. An anchoring means may optionally be provided at the distal end of the expansion member.

30 Claims, 8 Drawing Sheets

U.S. PATENT DOCUMENTS

| | | |
|---|---|---|
| 4,411,655 | 10/1983 | Schreck . |
| 4,479,497 | 10/1984 | Fogarty et al. . |
| 4,581,025 | 4/1986 | Timmermans . |
| 4,589,868 | 5/1986 | Dretler . |
| 4,601,713 | 7/1986 | Fuqua . |
| 4,650,466 * | 3/1987 | Luther ................................. 606/198 |
| 4,716,901 | 1/1988 | Jackson et al. . |
| 4,738,666 | 4/1988 | Fuqua . |
| 4,739,762 | 4/1988 | Palmaz . |
| 4,772,266 | 9/1988 | Groshong . |
| 4,798,193 | 1/1989 | Giesy et al. . |
| 4,846,791 | 7/1989 | Hattler et al. . |
| 4,865,593 | 9/1989 | Ogawa et al. . |
| 4,869,717 | 9/1989 | Adair . |
| 4,888,000 | 12/1989 | McQuilkin et al. . |
| 4,896,669 | 1/1990 | Bhate et al. . |
| 4,899,729 | 2/1990 | Gill et al. . |
| 4,921,479 | 5/1990 | Grayzel . |
| 4,955,895 | 9/1990 | Sugiyama et al. . |
| 4,972,827 | 11/1990 | Kishi et al. . |
| 4,986,830 | 1/1991 | Owens et al. . |
| 5,112,304 | 5/1992 | Barlow et al. . |
| 5,116,318 | 5/1992 | Hillstead . |
| 5,122,122 | 6/1992 | Allgood . |
| 5,139,511 | 8/1992 | Gill et al. . |
| 5,183,464 | 2/1993 | Dubrul et al. . |
| 5,201,756 | 4/1993 | Horzewski et al. . |
| 5,222,971 | 6/1993 | Willard et al. . |
| 5,234,425 | 8/1993 | Fogarty et al. . |
| 5,250,025 | 10/1993 | Sonsnowski et al. . |
| 5,431,676 * | 7/1995 | Dubrul et al. ...................... 606/185 |
| 5,460,170 | 10/1995 | Hammerslag . |
| 6,080,174 * | 6/2000 | Dubrul et al. ...................... 606/185 |

OTHER PUBLICATIONS

Product brochure BLUNTPORT, Auto Suture Company, a Division of United States Surgical Corporation (1992) 2 pages.

Product brochure DEXIDE® Inc., Dexide, Inc. (1992) 1 page.

* cited by examiner

TROCAR SYSTEM HAVING EXPANDABLE PORT

This application is a continuation of, and claims the benefit of priority from application Ser. No. 08/424,696, filed on Apr. 19, 1995, (now U.S. Pat. No. 6,080,174) which is a division of application Ser. No. 08/026,922; filed Mar. 5, 1993 (now U.S. Pat. No. 5,431,676) the full disclosures of which are incorporated herein by reference.

BACKGROUND OF THE INVENTION

1. Field of the Invention

The present invention relates generally to apparatus and methods for providing percutaneous access to an internal operative site during a surgical procedure. More particularly, the present invention relates to a trocar system which can be percutaneously introduced while in a narrow diameter configuration and which after introduction can be radially expanded to accommodate passage of larger diameter surgical instruments.

Minimally invasive surgical procedures rely on obtaining percutaneous access to an internal surgical site using small-diameter access tubes (typically 5 to 12 mm), usually referred to as trocars, which penetrate through the skin and which open to the desired surgical site. A viewing scope is introduced through one such trocar, and the surgeon operates using instruments introduced through other appropriately placed trocars while viewing the operative site on a video monitor connected to the viewing scope. The surgeon is thus able to perform a wide variety of surgical procedures requiring only several 5 to 12 mm punctures at the surgical site. Patient trauma and recovery time are thus greatly reduced.

Particular minimally invasive surgical procedures are often referred to based on the type of scope used to view the region of the body which is the operative site. Thus, procedures in the abdominal area, which rely on a laparoscope for viewing, are referred to as laparoscopic procedures. In such laparoscopic procedures, the patient's abdominal region is typically insufflated (filled with pressured carbon dioxide or nitrogen gas) to raise the abdominal wall and create sufficient operating space to perform a desired procedure. The trocars used in laparoscopic procedures must therefore include a valve at their proximal end to allow passage of the scope or surgical instruments while inhibiting leakage of the insufflating gas. It has also been proposed to perform laparoscopic procedures by mechanically expanding the abdomen rather than using insufflation.

Other minimally invasive surgical procedures include thoracoscopic procedures performed in the region of the chest, arthroscopic procedures performed in body joints, particularly the knee, gynecological laparoscopic procedures, and endoscopic surgical procedures performed in various regions of the body, typically with a flexible scope. These latter procedures do not normally employ pressurization and the trocars used generally do not include pressure valves at their proximal ends.

The design of suitable trocars must fulfill many requirements, particularly for those used in laparoscopic procedures in a pressurized environment. All trocars should be introducible to the patient with minimum trauma and with minimum risk of injury to internal organs. The trocars used in laparoscopic procedures should be readily sealable to inhibit the leakage of gas form the abdomen, and in particular should be designed to inhibit leakage in the region surrounding the external periphery of the trocar which passes through the abdominal wall. It is further desirable that trocars have means for anchoring within the percutaneous passage, and it would be particularly desirable if a single trocar could accommodate instruments having a wide variety of cross-sectional shapes and sizes.

Heretofore, trocar designs have met the above listed requirements with mixed results. The accommodation of various sized instruments has been met by providing trocars having different fixed diameters. Often, a surgeon will introduce the largest sized trocar, usually 10 to 12 mm, which can then accommodate most or all instruments (which are sized within this maximum) using a rubber adapter. While such an approach is feasible, the introduction of larger sized trocars exposes the patient to greater trauma and risk of injury than would be the case if smaller trocars were used.

External sealing about the periphery of the trocar has also not been adequately addressed. Certain trocar designs employ a tapered helical thread about their periphery. The thread is useful for anchoring, but greatly enlarges the trocar puncture in order to seal against the loss of pressurized insufflation gas. Other anchors, such as malecot structures have been employed on the distal end of the trocars, and are effective for anchoring but provide little sealing against the loss of pressure.

For these reasons, it would be desirable to provide trocars suitable for use in laparoscopic and other minimally invasive surgical procedures which can be easily introduced to the patient via a relatively small puncture (preferably less than 5 mm), which can then be radially expanded (and optionally subsequently reduced) to accommodate a wide variety of instrument sizes, and which provide for improved sealing about the trocar periphery and anchoring within the target site of the operative procedure.

2. Description of the Background Art

U.S. Pat. No. 5,183,464, assigned to the assignee of the present invention, describes a radially expandable dilator including an elongate dilation tube which receives an elongate expansion tube. European Patent Application 385 920 describes a variable diameter braid structure intended for capturing and removing stenotic material from blood vessels. U.S. Pat. No. 5,122,122, describes a trocar sleeve having a malecot structure at its distal end. Trocars for use in laparoscopic procedures are commercially available from suppliers such as United States Surgical Corp., Norwalk, Conn.; Endomed division of Cooper Surgical, Inc., Shelton, Conn.; and Dexide Inc., Fort Worth, Tex.

U.S. Pat. No. 4,738,666, describes an expandable catheter having an external sheath which is perforated to facilitate removal as the catheter is being expanded. U.S. Pat. No. 4,601,713, describes a variable diameter catheter having an inflatable retention balloon at its distal end. The catheter is introduced with an internal stylet which holds the catheter in a collapsed (reduced diameter) configuration. Removal of the stylet allows the catheter to expand. U.S. Pat. No. 4,141,364, describes an expandable endotracheal tube which is inserted in a collapsed configuration and springs back to an expanded configuration when air is introduced. Inflatable dilator apparatus are described in U.S. Pat. Nos. 4,589,868 and 2,548,602. Catheters having expandable structures are described in U.S. Pat. Nos. 4,986,830; 4,955,895; 4,896,669; 4,479,497; and 3,902,492.

U.S. Pat. No. 4,772,266, describes a dilator/sheath assembly that may be passed over an in-dwelling guide wire in order to enlarge an access hole, with entry of the sheath further enlarging the hole. U.S. Pat. No. 1,213,001, describes a trocar and cannula assembly which includes an intermediate tube to form a three-piece structure. U.S. Pat.

No. 3,742,958, discloses a cannula having an axial slot to allow the cannula to be stripped from a working catheter which has been introduced through the cannula. U.S. Pat. Nos. 4,888,000; 4,865,593; 4,581,025; 3,545,443; and 1,248,492, each describe devices suitable for percutaneous penetration of a body cavity, blood vessel, or solid tissue. The disclosures of each of the U.S. Patents cited in this paragraph are hereby incorporated herein by reference.

U.S. Pat. No. 4,899,729, describes an expansible cannula which includes a coiled conical sheath which can be percutaneously introduced and thereafter expanded by advancing an internal cylinder. U.S. Pat. No. 4,716,901 discloses an expandable trocar (not including a trocar valve) comprising a pair of opposed components having sharpened distal tips and covered by an elastic sleeve over a proximal portion thereof. U.S. Pat. No. 4,846,791, describes a multi-lumen catheter which includes an elastic outer sleeve and an internal divider which, when inserted, expands the sleeve. See also U.S. Pat. Nos. 668,879; 3,789,852; 4,411,655; 4,739,762; 4,798,193; 4,921,479; 4,972,827; 5,116,318; and 5,139,511, which were made of record in U.S. Pat. No. 5,183,464, assigned to the assignee of the present invention.

A dilator assembly including a guide member having an anchor at its distal end is described in copending application Ser. Nos. 07/616,122 and 07/913,129, assigned to the assignee of the present invention, the disclosures of which are incorporated herein by reference. A peel away sheath is described in copending application Ser. No. 07/967,602, assigned to the assignee of the present invention, the disclosure of which is incorporated herein by reference.

SUMMARY OF THE INVENTION

According to the present invention, improved apparatus and methods for forming and enlarging percutaneous penetrations into target locations within a patient's body are provided. The apparatus comprises an elongate dilation member including a radially expandable tubular braid and an elongate expansion member which is received in an axial lumen of the elongate dilation member to radially expand the braid and provide an enlarged access lumen therethrough. The elongate dilation member further includes a puncturing means near its distal end, typically being an elongate penetrating element having a sharpened distal tip which is removably received in and extends distally from the axial lumen of the braid. The elongate dilation member may thus be percutaneously introduced by puncturing the skin. The penetrating member is then removed to permit introduction of the elongate expansion member. The elongate expansion member includes a fixed-radius tubular element having an axial lumen which defines the desired access path.

The expanded braid of the elongate dilation member provides both an anchoring function and a sealing function. The tubular braid, which is preferably in the form of a mesh formed from non-elastic polymeric, stainless steel, or other filaments, shortens as it is radially expanded, causing the braid to tighten or clamp on the tissue with which it is in contact. Such tightening of the braid, when combined with the radial expansion, prevents separation of the tissue layers, provides excellent anchoring of the elongate dilation member within the percutaneous penetration, and enhances the peripheral sealing to inhibit loss of insufflation pressure utilized in laparoscopic procedures. A further advantage of the tubular braid in the elongate dilation member is that it will remain in place as the elongate expansion member is withdrawn therefrom. Thus, elongate expansion members having different cross-sectional areas and geometries can be introduced and withdrawn into the lumen of the tubular braid, thus allowing the cross-sectional area of the access lumen to be changed as desired. Tissue over the exterior of the braid will be able to stretch or relax, as appropriate, to accommodate such changes in diameter of the braid.

In a preferred aspect of the present invention, the elongate dilation member further comprises a removable protective sheath formed over the braid to facilitate the initial percutaneous introduction. After the elongate dilation member is in place, the protective sheath can be removed, either before, during, or after expansion of the tubular braid. In an exemplary embodiment, the removable sheath is axially split as the tubular braid is radially expanded, and the split portions of the sheath removed after expansion.

In a second preferred aspect of the present invention, the elongate expansion member further includes a rod having a tapered distal end removably received in the axial lumen of the fixed-radius tubular element. The tapered end extends distally from the tubular element, thus facilitating introduction of the expansion member through the axial lumen of the tubular braid. The rod can be withdrawn from the tubular element after it has been introduced through the braid, leaving the lumen of the tubular element available as the desired percutaneous access path.

In a further preferred aspect of the present invention, the elongate expansion member will include means for attaching a trocar valve at its proximal end. Typically, the trocar valve will be removably attached to the expansion member, permitting the same trocar valve to be used on different elongate expansion members having different cross-sectional areas, as they are exchanged during a procedure.

In a further preferred aspect of the present invention, the elongate penetrating element is a needle having a retractable obturator at its distal end. The obturator retracts as the needle is penetrated through skin, and extends forwardly as soon as the needle enters the patient's body, thus helping to protect the patient against accidental injury from the needle. The exemplary needle is a Veress needle of a type commonly used in insufflation devices.

The present invention further provides an improved radially expandable dilator of the type including a radially expandable dilation member and an elongate expansion member which is insertable through an axial lumen of the dilation member. The improvement comprises an expandable dilation member including a radially expandable tubular braid covered by a removable sheath. The tubular braid preferably comprises an open mesh composed of a non-elastic polymeric or metallic filaments, whereby the braid will shorten as its radius is increased.

The present invention still further provides an improved trocar of the type having a fixed-radius tubular element and a trocar valve disposed at a proximal end of the tubular element. The improvement comprises providing a plurality of tubular elements having different fixed diameters and interchangeable means at their proximal ends for securing a trocar valve thereto. The trocar further comprises means defining a radially expandable axial lumen for selectively receiving and conforming to particular ones of said plurality of tubular elements, whereby the defining means may be percutaneously introduced to provide an access lumen for introducing and interchanging tubular members, with the trocar valve being selectively attached to the tubular element after it has been introduced. Preferably, the defining means comprises an elongate radially expandable tubular braid having means at its distal end for puncturing tissue as the braid is percutaneously advanced.

The method according to the present invention comprises penetrating an elongate dilation member through a body surface to a target location within a patient's body. Optionally, a cover may be removed from the dilation member to expose a radially expandable tubular braid having an axial lumen which extends from the body surface to the target location. A first fixed-radius tubular element is then inserted through the lumen of the tubular braid, whereby the tubular braid is expanded to anchor itself within the percutaneous penetration. The tubular element thus provides an access lumen having an enlarged cross-sectional area. Optionally, the method further comprises removing the first fixed-radius tubular element and inserting a second fixed-radius tubular element having a lumen with a different cross-sectional area than that of the first tubular element. In this way, access lumens having a desired cross-sectional area can be introduced at the same location while causing the patient minimum trauma. Tissue abrasion is reduced or eliminated by sliding the second tubular element through the tubular braid, and there is no need to form new percutaneous penetrations.

DESCRIPTION OF SPECIFIC EMBODIMENTS

Figure 1:
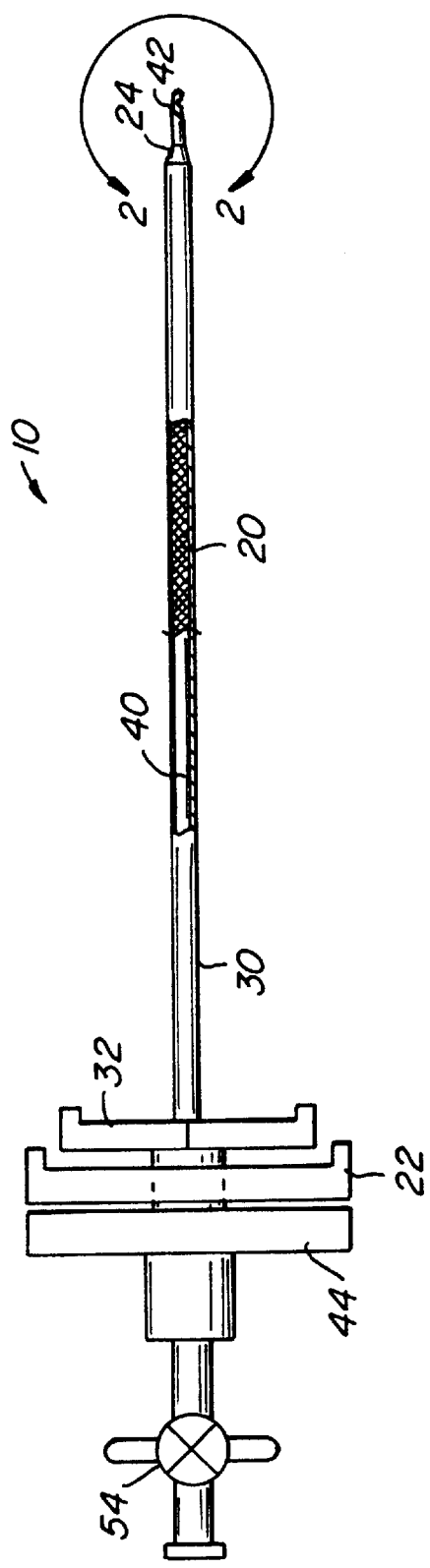
FIG. 1 is a side view of a first component of a trocar system constructed in accordance with the principles of the present invention. The first component includes an elongate dilation member having an elongate penetrating element received in an axial lumen thereof.

The present invention is useful for forming and enlarging percutaneous penetrations into a variety of target locations within a patient's body for a multiplicity of purposes. Such purposes include drainage, intra-organ drug administration, feeding, perfusion, aspiration, and the like, most usually being the introduction of viewing scopes and surgical instruments for use in minimally invasive surgical procedures, such as laparoscopic procedures, thoracoscopic procedures, arthroscopic procedures, endoscopic procedures, and the like.

The devices of the present invention are particularly valuable since they will create a very small initial penetration, usually being below about 5 mm, more usually being below about 4 mm, frequently being below about 3.5 mm, and preferably being 3 mm or below. The penetration will be subsequently enlarged to a desired final size, usually having a final diameter in the range from about 5 mm to 15 mm, more usually being from about 5 mm to 12 mm, and typically being from about 5 mm to 10 mm. The enlarged penetration will define an access lumen from the outside of the patient's body to the desired internal location, and it is a particular advantage of the present invention that the diameter of the access lumen can be changed as will be described in more detail hereinafter.

The dilation apparatus according to the present invention includes an elongate dilation tube having a distal end, a proximal end, and an axial lumen extending from the distal end to the proximal end. The dilation tube includes an expandable tubular braid which is initially in an elongated, narrow-diameter configuration. The braid may be open, but will often be laminated or covered with a coating or layer of elastic or plastically deformable material, such as silicone rubber, latex, polyethylene C-flex, or the like. The tubular braid is percutaneously introduced in its narrow-diameter configuration, and thereafter radially expanded using an elongate expansion member, as described in more detail hereinafter. The tubular braid is preferably formed as a mesh of individual non-elastic filaments (e.g., composed of polyamide fiber (Kevlar7, DuPont), stainless steel, or the like) so that radial expansion causes axial shortening of the braid. Such axial shortening as the braid filaments are radially penetrated into the surrounding tissue helps anchor the dilation member in place within the patient's tissue and helps seal the exterior of the dilation member against the tissue. Such a firmly anchored and gas-tight seal is a particular advantage in laparoscopic procedures.

The braid may be of conventional construction, comprising round filaments, flat or ribbon filaments, square filaments, or the like. Non-round filaments may advantageously reduce the axial force required to provide radial expansion. The filament width or diameter will typically be from about 0.002 inch to 0.25 inch, usually being from about 0.005 to 0.010 inch. Suitable braids may be obtained from a variety of commercial suppliers, such as Bently Harris, Lionville, Pa.; Manville Sealing Components, Denver, Colo.; and 3M Ceramic Materials, St. Paul, Minn. A particularly suitable braid is available under the tradename Exando7 PT from Bently-Harris.

The elongate dilation member may optionally further include a removable sheath covering the tubular braid. The sheath is usually composed of a lubricous material, such as a thin-walled flexible plastic, such as polyethylene, tetrafluoroethylene, fluorinated ethylenepropylene, and the like. The sheath protects the tubular braid during initial insertion of the dilation member, but is removed from the braid after the dilation member is in place. Preferably, the sheath will be weakened along an axial line to facilitate splitting of the sheath at some point during the procedure. Such removable sheaths will usually be employed only if the tubular braid does not itself include an elastic or deformable layer secured to the braid filament material. The construction of suitable sheaths is described in detail in copending application Ser. No. 07/702,642, assigned to the assignee of the present invention, the full disclosure of which is incorporated herein by reference.

The elongate dilation member will further comprise means at its distal end for puncturing tissue as the dilation member is percutaneously advanced. The puncturing means could be secured, either removably or permanently, to either the tubular braid, optional protective sheath, or both. In the exemplary embodiment, however, the puncturing means comprises a separate elongate penetrating element which is received in an axial lumen of the tubular braid, while the braid is in its axially elongate configuration. The penetrating means includes a sharpened distal tip which extends distally beyond the distal end of the tubular braid and optional cover sheath, thus facilitating penetration of the dilation member through the tissue.

In a particularly preferred embodiment, the penetrating element is a needle which includes an obturator which is retractably mounted therein and which extends distally beyond the sharpened distal tip. The obturator is usually spring-loaded, and will thus automatically retract as the needle is advanced through tissue and encounters significant tissue resistance to puncture. The obturator will, however, extend distally beyond the sharpened distal tip to protect the patient from injury after the dilation member has entered the desired target location, such as within the insufflated region of the abdomen during a laparoscopic procedure. Such needles are known as Veress needles and are commonly employed for insufflation in laparoscopic and other procedures.

The elongate dilation member may further comprise an anchor at its distal end to be deployed after penetration but prior to expansion. The anchor would serve to hold the dilation member in place and to prevent separation of the skin and fascial layers as the expansion member is introduced through the dilation member. Usually, however, the inherent anchoring capacity of the tubular braid is sufficient by itself to hold the dilation member in place and prevent tissue separation, so that the anchor will not be necessary.

The elongate expansion member includes a fixed-radius tubular element having a distal end, a proximal end, and an axial lumen extending therebetween. The axial lumen will have a cross-sectional area which is greater than that of the tubular braid in its non-radially expanded configuration. Thus, by introducing the expansion member through the lumen of the tubular braid and causing the braid to radially expand, an enlarged access channel will be provided by the lumen of the fixed-radius tubular element. To facilitate introduction of the elongate expansion member through the axial lumen of the tubular braid, a rod having a tapered distal end is preferably provided in the lumen of the tubular element. The tapered end extends distally from the tube and acts to spread apart the tubular braid as the expansion member is advanced. The rod can then be removed from the tube to leave the access lumen unobstructed after the expansion member has been fully advanced through the tubular braid. Trocar systems of the present invention will preferably include at least two elongate expansion members having different cross-sectional areas so that the same dilation member can be selectively used as a channel to introduce access ports of many different sizes.

The elongate expansion member may optionally include an anchoring means at or near its distal end. The anchoring means can take a variety of forms, including malecot structures, hooks, inflatable balloons, and the like, and will serve to hold the expansion member in place at the target location after deployment. To further enhance anchoring, an external clamp or anchor may further be provided at or near the proximal end of the expansion member so that tissue disposed between the anchors, e.g., the abdominal wall, may be captured therebetween. Anchoring provided by such clamping will, of course, be in addition to the inherent anchoring achieved by expansion of the tubular braid, as described above.

Usually, the elongate expansion member will include means at its proximal end for removably securing a trocar valve. The trocar valve is similar to conventional trocar valves which are fixedly mounted on trocars. The valve will include internal structure which permits the introduction of viewing scopes and/or surgical instruments having different cross-sectional areas, while sealing about the periphery of such devices to prevent loss of insufflation pressure in laparoscopic procedures. The valves will also typically include stopcocks which permit introduction or venting of insufflation gas, irrigation, aspiration, and the like. Conventional trocar valves are manufactured by various suppliers, such as Ethicon, Inc., Somerville, N.J.; United States Surgical Corporation, Norwalk, Conn.; Dexide, Inc., Fort Worth, Tex.; and others.

The length of the elongate dilation tube will vary depending on the intended usage, but will generally be in the range from about 10 cm to 25 cm. The length of dilation tubes intended for laparoscopic procedures will generally be in the range from about 10 cm to 20 cm, typically being in the range from about 10 cm to 15 cm. The length of dilation tubes used in trocar systems intended for thoracoscopic use will generally be shorter, typically having a length in the range from about 5 cm to 10 cm. The length of the elongate expansion member, of course, will generally be somewhat greater than that of the elongate dilation member, thus permitting radial expansion of the entire length of the dilation member.

Referring now to the figures, an exemplary trocar system constructed in accordance with the principles of the present invention will be described. The three principle components of the trocar system are an elongate dilation member 10, best illustrated in FIGS. 1–3, one or more elongate expansion members 12 and 14, best illustrated in FIGS. 4–8, and a trocar valve 16, best illustrated in FIG. 8. Each of these components, and the use of these components in the method of the present invention, will now be described in greater detail.

The elongate dilation member 10 comprises a tubular braid 20 having an axial lumen which extends from a handle 22 located at its proximal end to a ferrule 24 on the needle 40 located at its distal end. The braid 20 is attached to the proximal handle 22 in a manner that permits radial expansion of the braid as the expansion member 12 or 14 is subsequently introduced therethrough, as will be described in greater detail hereinafter. The tubular braid will include discrete braid filaments, as described above, and may further comprise a laminated elastomeric or plastically deformable layer, as described above. A passage 26 is formed in the proximal handle 22 in order to permit passage of the expansion members into the axial lumen of the tubular braid 20.

Figure 2:
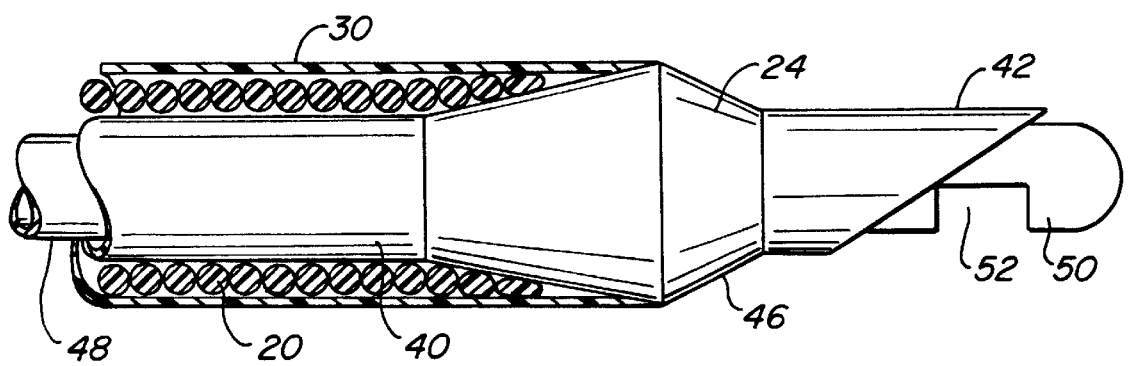
FIG. 2 is a detailed, cross-sectional view taken at region 2—2 of FIG. 1.
Figure 3:
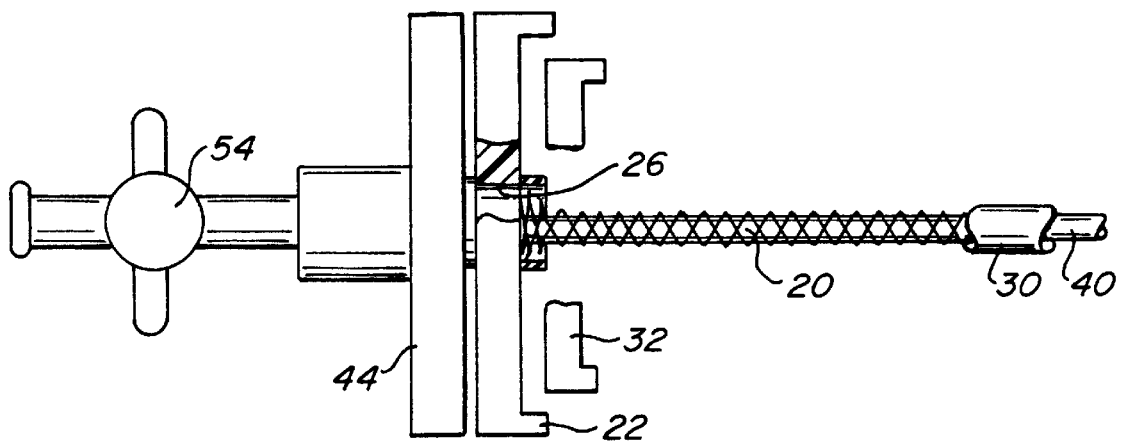
FIG. 3 is a detailed view of the proximal end of the component of FIG. 1, shown with portions broken away.

The tubular braid 20 is covered with a removable sheath 30 (in the illustrated embodiment) having a handle 32 at its proximal end. The sheath 30 extends the entire length of the tubular braid 20 and terminates at its proximal end, generally at the location of ferrule 24, as best illustrated in FIG. 2. The removable sheath 30 may be constructed as described in copending application Ser. No. 07/967,602, the full disclosure of which has been previously incorporated herein by reference.

A needle 40 having a sharpened distal tip 42 and a proximal handle 44 is initially received within the axial lumen of tubular braid 20. The ferrule 24 is secured near the sharpened distal tip 42 of the needle 20 and includes a forward tapered surface 46 (FIG. 2) which facilitates penetration of the elongate dilation member 10 through the patient's skin, fascial tissues, and organ walls. In particular, the ferrule 24 acts as a transition from the narrow diameter needle 40 to the slightly larger diameter removable sheath 30. The tubular braid 20 is received within an annular lumen which is defined between the outer surface of the needle 40 and the inner surface of the sheath 30. Alternatively, the distal end of the sheath 30 may itself be tapered in order to provide the desired smooth transition. It will thus be possible to eliminate the ferrule 24 in certain embodiments of the invention.

The needle 40 is preferably in the form of an insufflation needle having a protective element at its distal tip 42. As illustrated, the protective element is an obturator 48 having a blunt end 50 which is reciprocatably received in the axial lumen of the needle 40. The obturator 48 is spring-loaded so that the blunt end 50 extends distally from the sharpened distal tip 42 of the needle 40 in its shelf or "at rest" configuration. As the needle 42 is pressed firmly against the patient's skin or other tissue, however, the blunt end 50 will be retracted back into the needle 40 so that the sharpened tip 42 can penetrate. Usually, the obturator 48 will be hollow and include a port 52 at its distal end. By providing a valve assembly 54 at its proximal end, the combination of needle 40 and obturator 48 can be used to introduce or withdraw fluids, particularly being useful for performing the initial stages of insufflation. Insufflation needles which can be modified for use in the present invention are available from commercial suppliers, such as Ethicon, Inc., Somerville, N.J., (under the tradename Endopath7 Ultra Veress Needle) and United States Surgical Corporation, Norwalk, Conn. (available under the tradename Auto Suture7 Surgineedle7).

Figure 4:
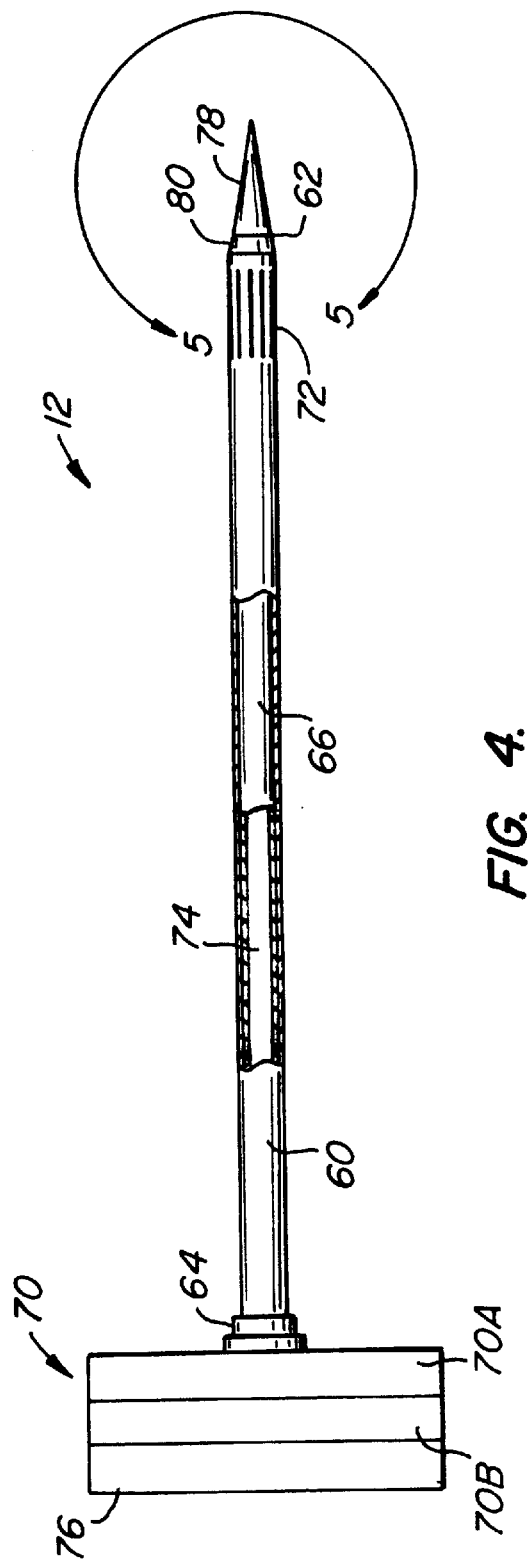
FIG. 4 illustrates a first elongate expansion member constructed in accordance with the principles of the present invention, which forms a second component of the trocar system of the present invention.
Figure 5:
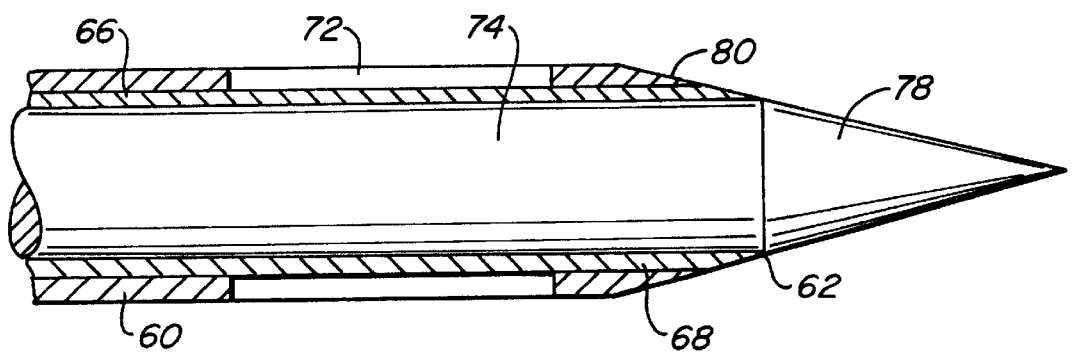
FIG. 5 is a detailed, cross-sectional view of the distal tip taken at line 5—5 in FIG. 4.
Figure 6:
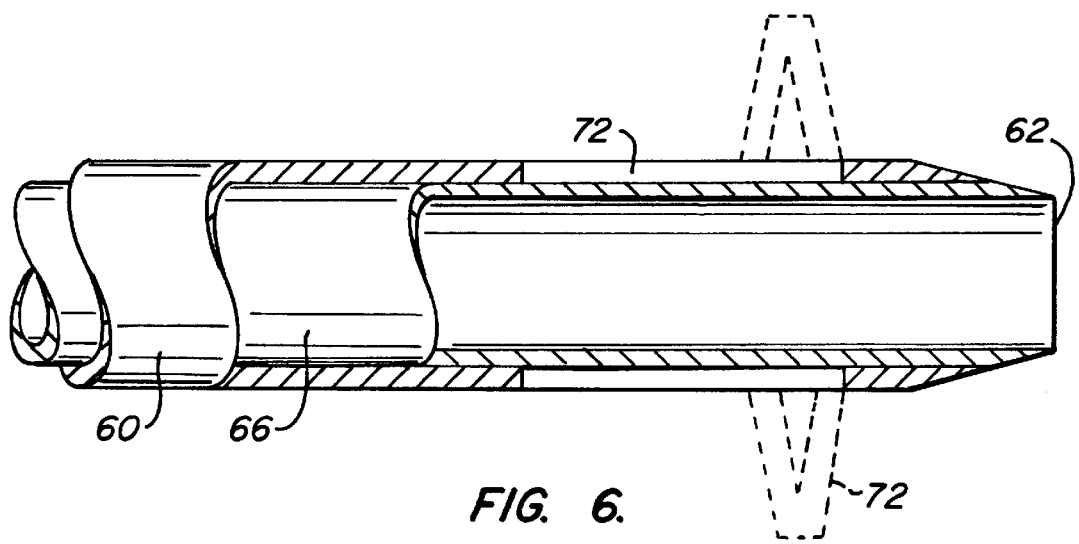
FIG. 6 is similar to FIG. 5, except that a rod having a tapered distal end has been removed from a lumen of the structure, with an expanded anchoring means shown in broken line.
Figure 7:
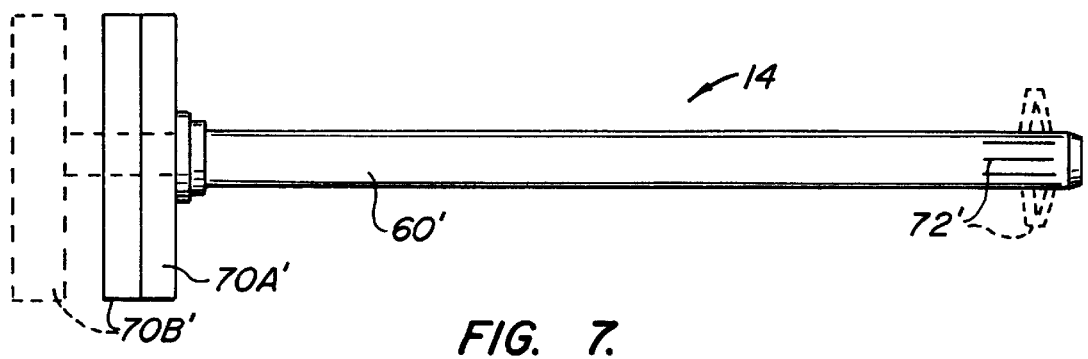
FIG. 7 illustrates a second elongate expansion member, similar to the first elongate expansion member of FIG. 4, except that it has a larger diameter. The expansion member of FIG. 7 is shown with an expanded anchoring member in broken line and with the inner tapered rod removed.

Referring now to FIGS. 4–6, the first elongate expansion member 12 will be described in detail. The expansion member 12 comprises a fixed-radius tubular element 60 having a distal end 62 and a proximal end 64. An inner coaxial tube 66 is slidably received within the axial lumen of the fixed-radius tubular element 60, being secured to the tubular element only at the distal end 68. A proximal handle 70 includes a distal half 70A which is secured to the proximal end of tubular element 60 and a proximal half 70B which is connected to the proximal end of the coaxial tube 66. Thus, the inner coaxial tube to be drawn proximally relative to the fixed-radius tubular element 60 by drawing the halves 70A and 70B axially apart (as shown in FIG. 7 with respect to a second embodiment of the expansion member). In this way, a malecot structure 72 formed near the distal end of the fixed-radius tubular element 60 may be expanded, as illustrated in broken line in FIG. 6.

The first elongate expansion member 12 further includes an internal obturator or rod 74 having a handle 76 at its proximal end and a tapered conical surface 78 at its distal end. The tapered conical surface 78 extends distally from the distal end 62 of the fixed-radius tubular element 60, as best illustrated in FIG. 5. The outer peripheral surfaces of both the fixed-radius tubular element 60 and inner coaxial tube 66 are chamfered to form a conical surface 80 which is aligned with the tapered conical surface 78 when the rod 74 is fully inserted within the expansion member 12. As will be seen hereinafter in connection with FIG. 9, the combination of the tapered conical surface 78 and tapered region 80 facilitates introduction of the expansion member 12 through the tubular braid 20 of the elongate dilation member 10.

Referring now to FIG. 7, a second elongate expansion member 14 is illustrated. The second expansion member 14 is similar in all respects to the first expansion member 12, except that the diameter of fixed-radius tubular element 60' is larger than that of the tubular element 60 of the first expandable member 12. The particular diameters of the expansion members are not critical, with exemplary ranges being set forth above. In the exemplary embodiment, the diameter of the first elongate expansion member 12 will typically be about 6 mm to 8 mm, to provide an access lumen of approximately 5 mm. The diameter of the second expansion member 14 will be about 12 mm to 14 mm, to provide an access lumen of about 10 mm. The use of 5 mm and 10 mm access lumens are conventional in laparoscopic surgery. It is a particular advantage of the present invention, however, that a wide variety of access lumen diameters can be provided. Thus, it will be expected that trocar systems may include two, three, four, or more expansion members with incrementally different diameters to accommodate virtually any scope or instrument which might be introduced.

FIG. 7 illustrates the expansion member 14 having the inner rod removed therefrom. After the inner rod is removed, the two halves 70A' and 70B' of the handle 70' may be drawn axially apart, as illustrated in broken line, in order to expand the malecot structure 72', as also illustrated in broken line.

Figure 8:
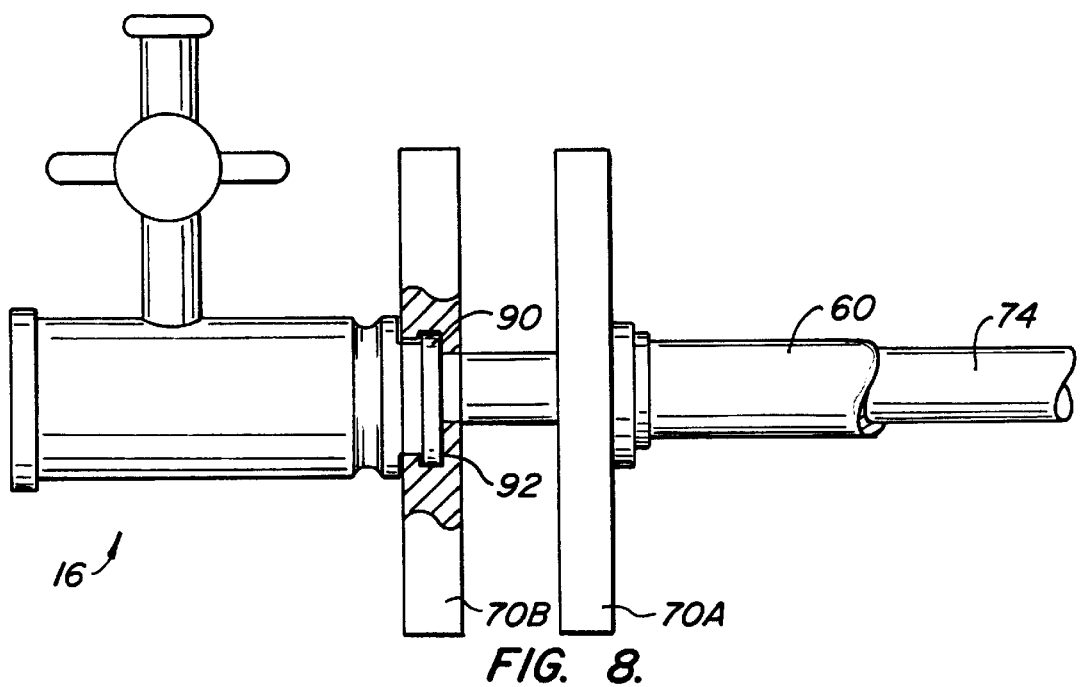
FIG. 8 is an enlarged view of the proximal end of the expansion member of FIG. 8, shown with portions broken away and with a trocar valve secured thereto.

Referring now to FIG. 8, the handle 70 of first expansion member 12 (as well as handle 70' of the second expansion member 14) will be constructed to removably receive the trocar valve 16. The trocar valve 16 will be of conventional construction, except that it will include a mounting means at its distal end. As illustrated in FIG. 8, the mounting means comprises a male bayonet mount 90 which is detachably received within a female bayonet receptacle 92 in the proximal half 70B of the handle 70. In this way, the trocar valve 16 can be mounted on different expansion members as they are exchanged within the tubular braid 20 of dilation member 10. This is a particular advantage since it reduces the cost and complexity associated with maintaining an inventory of trocars having dedicated valves on each diameter sheath.

Figure 9:
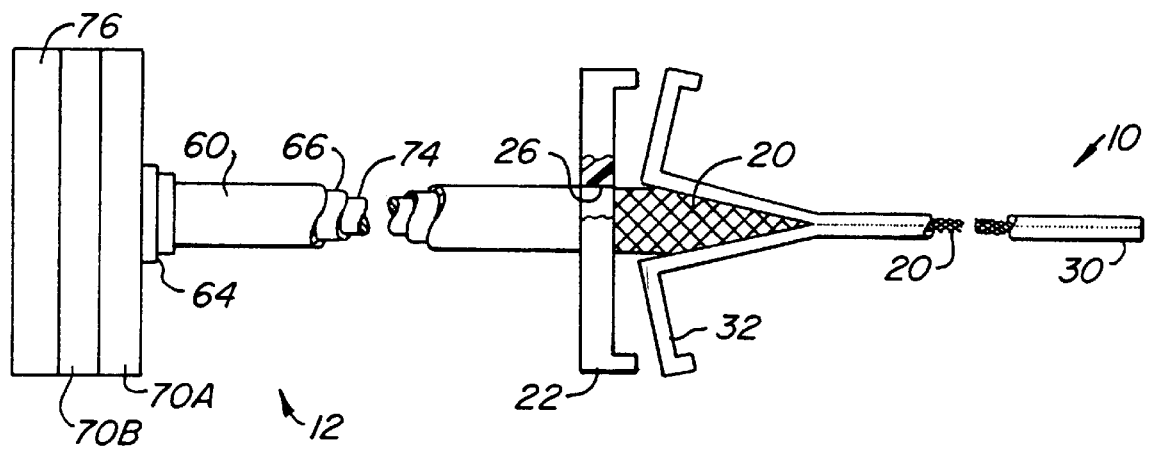
FIG. 9 illustrates the use of the elongate expansion member of FIGS. 4 or 7 for expanding the elongate dilation tube of FIG. 1 and splitting the sheath about the braid.
Figure 10:
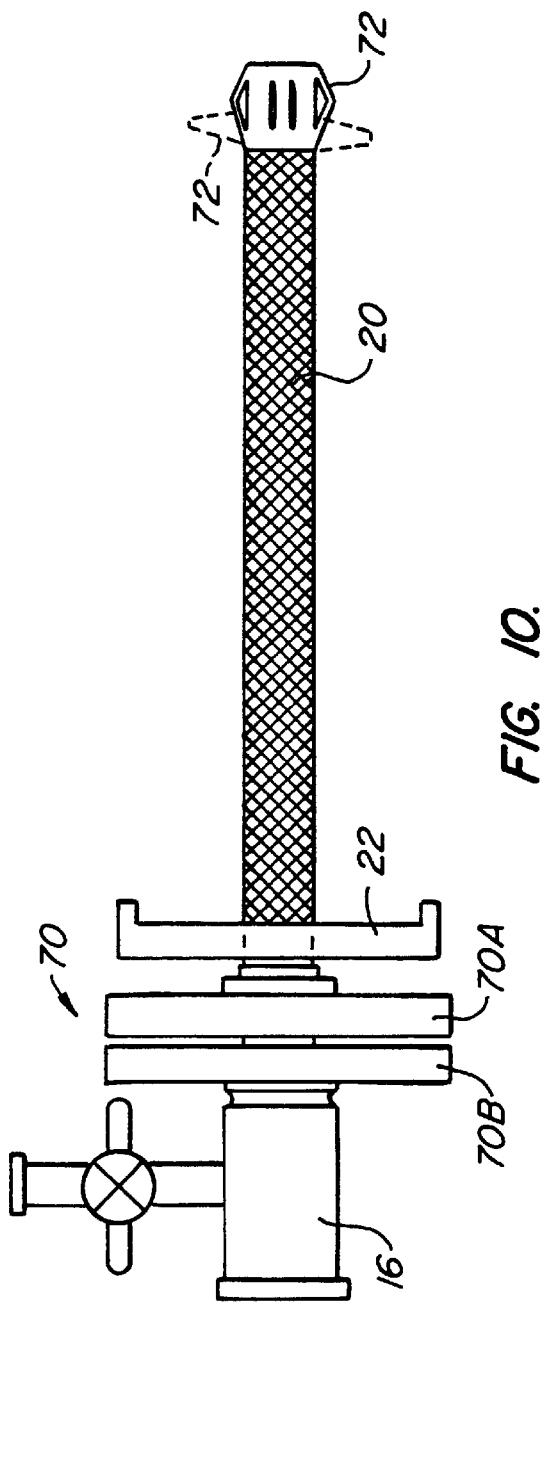
FIG. 10 illustrates the elongate dilation member of FIG. 9, shown after expansion and deployment of a distal anchoring means.

Referring now to FIGS. 9 and 10, insertion of elongate expansion member 12 through the elongate dilation member 10 will be described in more detail. Prior to introducing the expansion member 12, of course, the needle 40 will have been removed from the axial lumen of tubular braid 20 of the dilation member 10. The tapered distal end defined by surfaces 78 and 80 is introduced through the passage 26 in handle 22, and thus enters the axial lumen in tubular braid 20. The sheath 30 will optionally have been split by withdrawal of the needle 40 and passage of the ferrule 24 through the sheath. Alternatively, introduction of the expansion member 12 will axially split the sheath 30, as illustrated in FIG. 9. As can be seen, distal advancement of the dilation member 12 causes radial expansion of the tubular braid 20, eventually resulting in the fully expanded braid as illustrated in FIG. 10 (where the inner rod 74 has been removed).

After the expansion member 12 is fully inserted, the (undeployed) malecot structure 22 will extend distally from the distal end of the tubular braid, as illustrated in FIG. 10. The sheath 30 (which will have been split by passage of the expansion member therethrough) will then be withdrawn using handle 32, and the inner rod 74 will be withdrawn using handle 76. The halves 70A and 70B of handle 70 will then be drawn axially apart to deploy the malecot structure 72. The trocar valve 16 will then be mounted on the proximal half 70B of the handle 70, and the structure will be generally as illustrated in FIG. 10. Note that it is the fixed-radius tubular element 60 which provides the structural support within the expanded tubular braid 20. It is also the axial lumen within the fixed-radius tubular element 60 which provides the desired access channel from the trocar valve 16 to the distal end of the structure.

Figure 11:
FIGS. 11 and 12 illustrate the tubular braid of the elongate dilation member in the radially non-expanded and radially expanded configurations, respectively.
Figure 12:
Figure 12A:
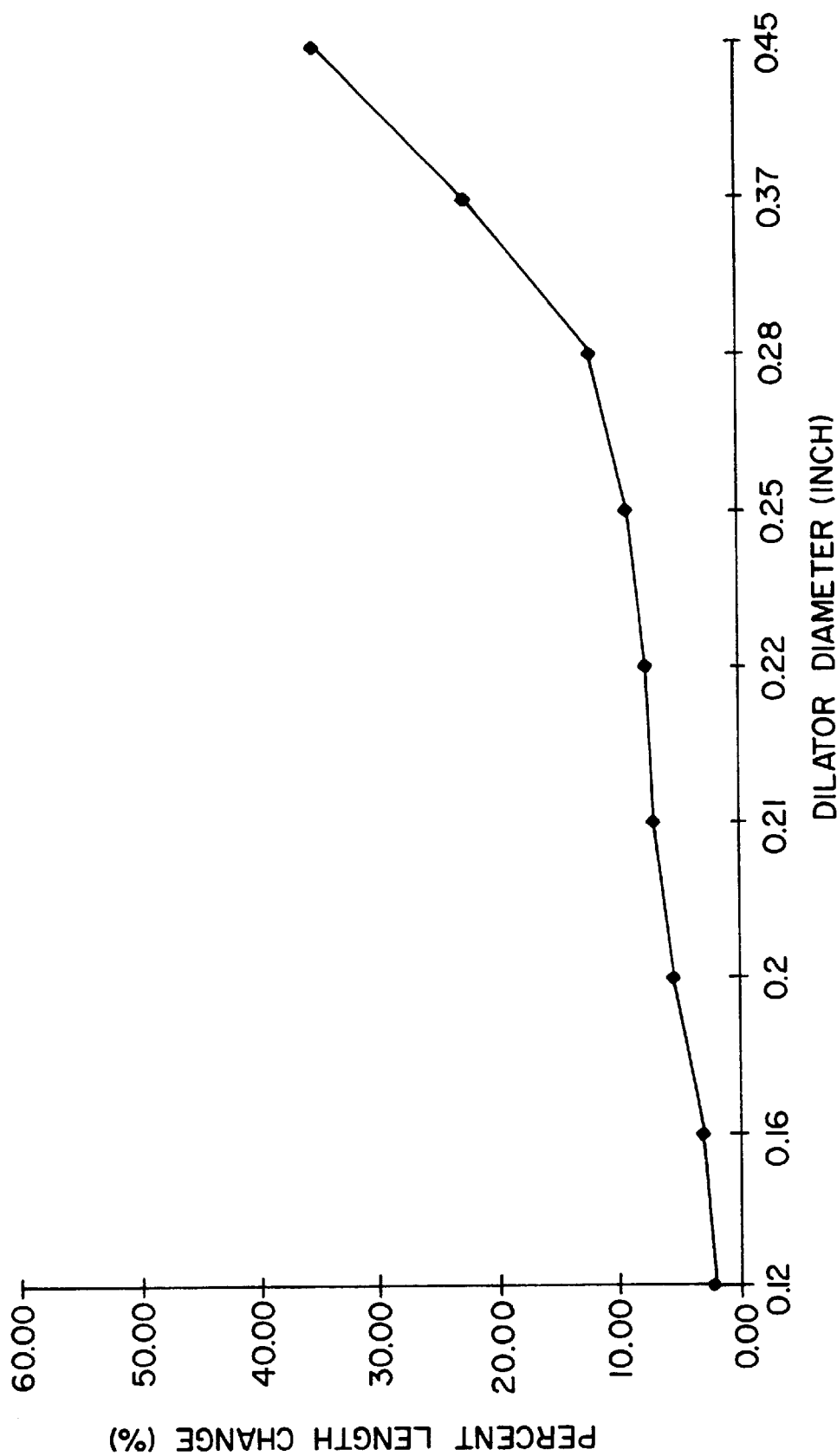
FIG. 12A is a graph illustrating the degree of shortening of the tubular braid of FIGS. 11 and 12 as a function of radial expansion.
Figure 13:
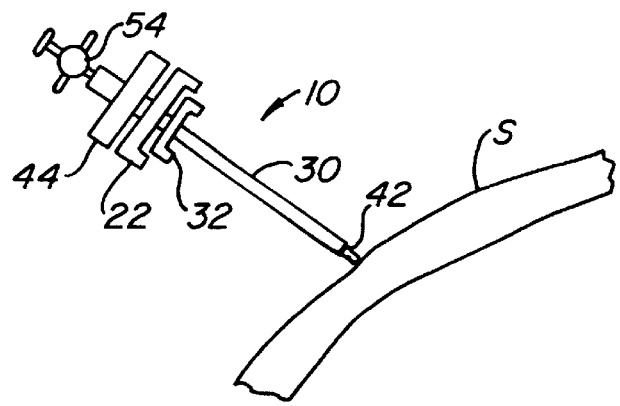
FIGS. 13–20 illustrate use of the trocar system of the present invention in forming and enlarging a percutaneous penetration.

Referring now to FIGS. 11 and 12, the expansion of tubular braid 20 from its initial narrow-diameter configuration illustrated in FIG. 11 to its radially expanded configuration illustrated in FIG. 12 will be described. FIG. 12A illustrates the percentage shortening effect as the exemplary Expando7 PT braid is radially expanded from about 0.1 inch to 0.45 inch.

Figure 14:
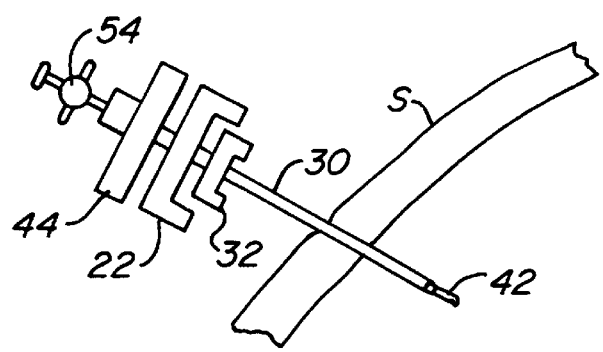

Referring now to FIGS. 13–20, use of the exemplary trocar system of the present invention for performing a percutaneous penetration will be described. The elongate dilation member 10 is initially positioned at a location on the patient's skin S where it is desired to form the penetration. The dilation member 10 is then penetrated through the skin S by advancing the sharpened distal tip 42 of the needle 40 (FIG. 1) through the skin, as illustrated in FIG. 14. In the case of laparoscopic procedures, as soon as the sharpened tip 42 of the needle 40 penetrates through the skin into the abdomen, the blunt end 50 of obturator 48 will automatically extend to protect the patient's internal organs from accidental injury. At this point, the lumen of needle 40 may be used for insufflation if desired.

Figure 15:
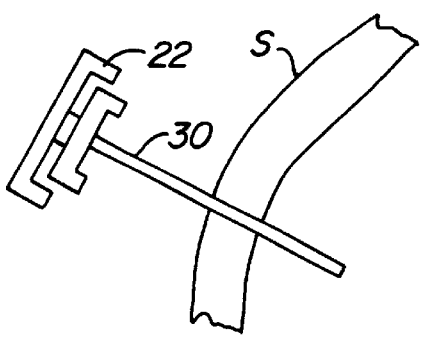

After the dilation member 10 has been advanced to its desired location, the needle 40 will be withdrawn using handle 44, leaving the sheath 30 (which may have been split by withdrawal of the needle 40 and attached ferrule 24) and the tubular braid therein with handle 22 at its proximal end, as illustrated in FIG. 15.

Figure 16:
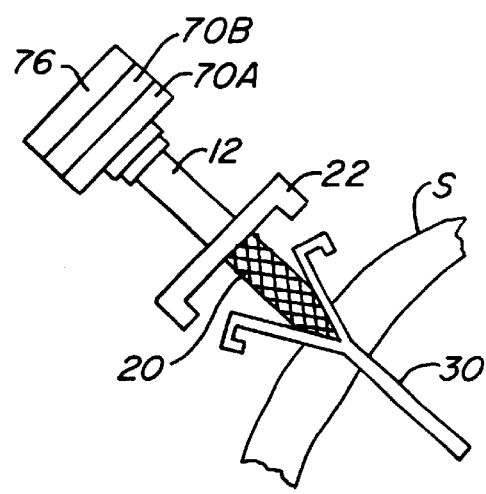

Elongate expansion member 12 is next introduced through the passage 26 in handle 22, thus expanding the tubular braid 20 and splitting the sheath 30 (if not already accomplished), as illustrated in FIG. 16. The presence of the sheath 30 and braid 20 facilitates radial expansion of the penetration which has been formed through the skin S, as illustrated in FIG. 16.

Figure 17:
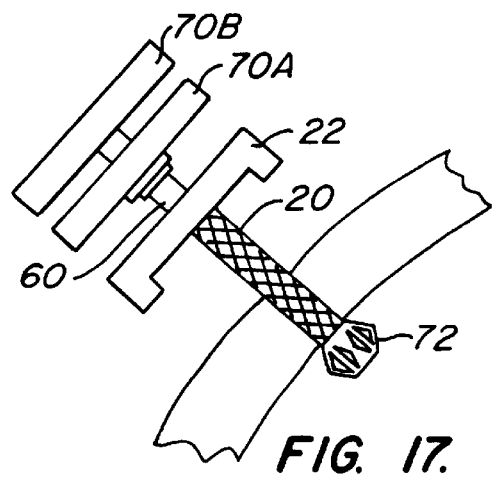
Figure 18:
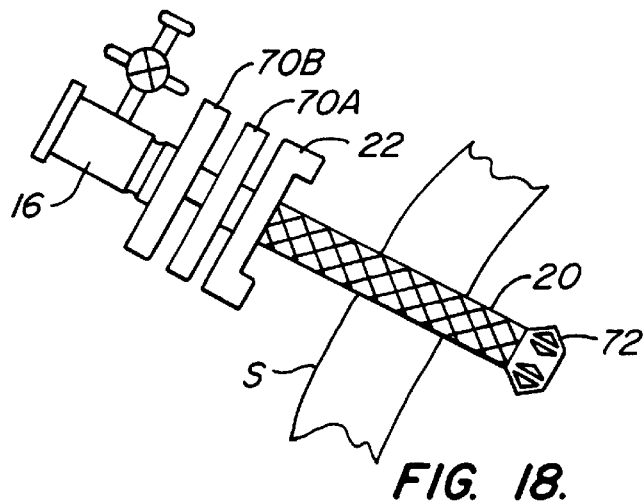

After the expansion member 12 has been fully inserted through the dilation member 10, the inner coaxial rod 66 will be withdrawn from the fixed-radius tube 60, and the sheath 30 will be withdrawn from over the expanded tubular braid, as illustrated in FIG. 17. The malecot structure 72 will be expanded by drawing halves 70A and 70B axially apart, as illustrated in FIG. 17. Trocar valve 16 may then be secured to the proximal half 70B of handle 70, as illustrated in FIG. 18.

Figure 19:
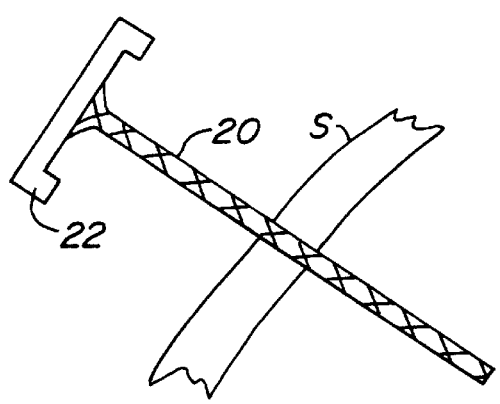
Figure 20:
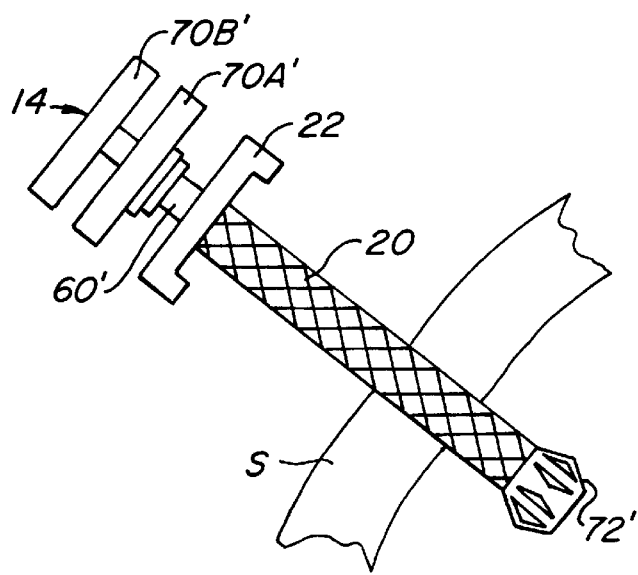

If it is desired to change the diameter of the access channel of the expansion member, the first expansion member 12 may be withdrawn from the tubular braid, as illustrated in FIG. 19. The tubular braid 20 will at least partially collapse, but will still provide an internal lumen to permit introduction of a second expansion member, such as the larger diameter second expansion member 14. The second expansion member 14 may be introduced through the handle 22 in a manner analogous to introduction of the first expansion member 12, except that the sheath 30 will no longer be in place. The tubular braid 20, however, is sufficient by itself to permit the passage of the expansion member 14 through the percutaneous penetration through skin S with minimum trauma to the patient. It will be appreciated that expansion members having smaller or larger diameters may be exchanged for the initially present expansion member in the tubular braid 20. Final placement of second expansion member 14 is illustrated in FIG. 20, where the malecot structure 72' has been deployed by pulling the handle 70' proximally relative to fixed radius tube 60'.

Although the foregoing invention has been described in some detail by way of illustration and example, for purposes of clarity of understanding, it will be obvious that certain changes and modifications may be practiced within the scope of the appended claims.

What is claimed is:

1. An apparatus for forming and enlarging a percutaneous penetration, said apparatus comprising:
   an elongate dilation member including a radially expandable tubular braid and having a proximal end, a distal end, and an axial lumen with a first cross-sectional area;
   means at the distal end of the dilation member for puncturing tissue as the member is percutaneously advanced;
   an elongate expansion member including a fixed-radius tubular element having a distal end, a proximal end, and an axial lumen with a second cross-sectional area; and
   means at the distal end of the expansion member for facilitating insertion of the tubular element through the axial lumen of the dilation member.

2. An apparatus as in claim 1, wherein the elongate dilation member further includes a removable sheath formed over the expandable tubular braid, wherein the sheath covers the braid while the dilation member is percutaneously advanced and can thereafter be removed to expose the braid to penetrated tissue.

3. An apparatus as in claim 1, wherein the tissue puncturing means comprises an elongate penetrating element having a sharpened distal tip and being removably received within the axial lumen of the dilation member with the sharpened distal tip extending distally therefrom.

4. An apparatus as in claim 1, wherein the elongate expansion member further includes an expandable anchor near its distal end.

5. An apparatus as in claim 1, wherein the means for facilitating insertion includes a rod having a tapered distal end removably received in the axial lumen of the expansion member, wherein the tapered end extends distally from the expansion member when the rod is fully inserted therein.

6. A radially expandable trocar system comprising:
   an elongate dilation member having a proximal end and a distal end and including a radially expandable tubular braid having an axial lumen with a first cross-sectional area;
   an elongate penetrating element having a proximal end and a sharpened distal tip, wherein said penetrating element is removably received within the axial lumen of the braid with the sharpened distal tip extending distally from the distal end of the elongate dilation member;
   a first elongate expansion member having a proximal end and a tapered distal end, and including a fixed-radius tubular element having an axial lumen with a cross-sectional area greater than that of the tubular braid; and
   a trocar valve removably attachable to the proximal end of the elongate expansion member so that said valve is disposed at the proximal end of the axial lumen in the fixed-radius tubular element.

7. A trocar system as in claim 6, wherein the radially expandable tubular braid comprises a mesh composed of non-elastic filaments, whereby the braid will shorten as its radius is increased.

8. A trocar system as in claim 7, wherein the elongate dilation member further includes a removable sheath over the tubular braid and wherein the expandable tubular braid is attached to a first handle at its proximal end and the removable sheath is attached to a second handle at its proximal end, wherein the second handle is located distally of the first handle to permit removal of the sheath over the braid using the second handle.

9. A trocar system as in claim 8, wherein the removable sheath is a cylindrical polymeric tube which is axially scored on opposite sides or on one side only and wherein the second handle is weakened at locations aligned with the axial scores on the polymeric tube, to permit splitting of the sheath and handle to facilitate removal of the sheath.

10. A trocar system as in claim 7, wherein the tubular braid of the dilation member is a laminated structure comprising the braid filaments in an elastic or plastically deformable matrix layer.

11. A trocar system as in claim 6, wherein the elongate penetrating element is a needle having a retractable obturator at its distal end.

12. A trocar system as in claim 6, wherein the elongate expansion member further includes a rod having a tapered distal end removably received in the axial lumen of tubular element, wherein the tapered distal end extends distally from the tubular element when the rod is fully received therein.

13. A trocar system as in claim 12, wherein the fixed-radius tubular element further includes an expandable anchor near its distal end.

14. A trocar system as in claim 6, wherein the elongate expansion member further includes at its proximal end a connector open to the lumen of the expansion member for detachably securing the trocar valve.

15. A trocar system as in claim 14, wherein the connector is a bayonet fitting.

16. A trocar system as in claim 6, wherein the trocar valve comprises a valve body having a body with an axial passage, valve means in the axial passage for inhibiting loss of pressure through said passage, and means on the body aligned with the axial passage for removably securing the body to the proximal end of the elongate expansion member.

17. A trocar system as in claim 6, further comprising at least one additional elongate expansion member, a proximal end, and a tapered distal end, and including a fixed-radius tubular element having an axial lumen with a cross-sectional area greater than that of the tubular braid and different from that of the first elongate expansion member.

18. An improved trocar of the type including a fixed-radius tubular element having a trocar valve at a proximal end thereof, wherein the improvement comprises:

a plurality of tubular elements having different fixed diameters and means for detachably securing the trocar valve thereto; and means defining a radially expandable axial lumen for selectively receiving and conforming to said plurality of tubular elements, whereby said defining means may be percutaneously introduced to provide an access lumen for introducing and interchanging tubular members with the trocar valve being selectively attached to each tubular element after it has been introduced.

19. An improved trocar as in claim 18, wherein the defining means comprises an elongate radially expandable tubular braid and means at a distal end of the braid for puncturing tissue as the braid is percutaneously advanced.

20. An improved trocar as in claim 19, wherein the puncturing means comprises an elongate penetrating element having a sharpened distal tip and being removably received within an axial lumen of the elongate radially expandable tubular braid.

21. An improved trocar as in claim 20, wherein each tubular element includes a rod received in an axial lumen thereof, wherein the rod has tapered distal end which extends distally from a distal end of the tubular element to facilitate insertion into the axial lumen of the elongate radially expandable tubular braid.

22. A method for forming and enlarging a percutaneous penetration to a target location within a patient's body, said method comprising:

penetrating an elongate dilation member through tissue to the target location wherein the dilation member includes a tubular braid formed of a mesh of non-elastic filaments which axially shorten as they are radially expanded; and inserting a first fixed-radius tubular element through a lumen of the tubular braid, wherein the lumen of the tubular element has a cross-sectional area greater than that of the lumen of the tubular braid and whereby shortening of the mesh anchors the dilation member in the tissue.

23. A method as in claim 22, further comprising:

removing the first fixed-radius tubular element from the lumen of the tubular braid, wherein the braid radially collapses but remains generally axially fixed;

inserting a second fixed-radius tubular element through the lumen of the tubular braid, wherein the cross-sectional area of the second fixed-radius tubular element is different than that of the first fixed-radius tubular element.

24. A method as in claim 23, wherein the cross-sectional area of the second tubular element is greater than that of the first tubular element.

25. A method as in claim 23, wherein the cross-sectional area of the second tubular element is less than that of the first tubular element.

26. A method as in claim 22, wherein the elongate dilation member comprises a cover disposed over the tubular braid and wherein the method further comprises removing the cover to expose the braid prior to inserting the tubular element.

27. A method as in claim 26, wherein the cover is a thin-walled sheet composed of a polymeric material which is removed by splitting apart, peeling away, and withdrawing from the tubular braid.

28. A method as in claim 22, wherein the elongate dilation member comprises an elongate penetrating element having a sharpened distal tip removably received within and extending distally from the axial lumen of the expandable tubular braid, further comprising the step of removing the elongate penetrating element from the braid after penetrating the dilation member and before inserting the first fixed-radius tubular element.

29. A method as in claim 22, wherein the first fixed-radius tubular element includes a rod having a tapered distal end removably received in an axial lumen thereof, wherein the tapered distal end extends distally from the tubular element to facilitate insertion through the axial lumen of the tubular braid, further comprising removing the rod from the tubular element to leave an access channel.

30. A method as in claim 22, wherein the mesh of the tubular braid is laminated in an elastic or plastically deformable matrix.

* * * * *